US00PP28188P2

(12) United States Plant Patent
Larsen

(10) Patent No.: US PP28,188 P2
(45) Date of Patent: Jul. 11, 2017

(54) ***OSTEOSPERMUM* PLANT NAMED 'SUNOST1502'**

(50) Latin Name: *Osteospermum ecklonis*
Varietal Denomination: SUNOST1502

(71) Applicant: SUNNY GRONNEGYDEN APS, Odense N. (DK)

(72) Inventor: Bjarne Nyholm Larsen, Odense N. (DK)

(73) Assignee: SUNNY GRONNEGYDEN APS, Odense N (DK)

( * ) Notice: Subject to any disclaimer, the term of this patent is extended or adjusted under 35 U.S.C. 154(b) by 0 days.

(21) Appl. No.: 14/998,428

(22) Filed: Dec. 31, 2015

(51) Int. Cl.
*A01H 5/02* (2006.01)

(52) U.S. Cl.
USPC ..... Plt./360

(58) Field of Classification Search
USPC ..... Plt./360
See application file for complete search history.

(56) References Cited

PUBLICATIONS

UPOV hit on *Osteospermum* plant named 'Sunost1502', QZ PBR 20152180, published Dec. 15, 2015.*

* cited by examiner

*Primary Examiner* — Anne Grunberg
(74) *Attorney, Agent, or Firm* — C. A. Whealy

(57) ABSTRACT

A new and distinct cultivar of *Osteospermum* plant named 'SUNOST1502', characterized by its upright and mounding plant habit; freely branching growth habit; freely flowering habit; large daisy-type inflorescences with dark orange red-colored ray florets with that are dark red in color towards the base; and good garden performance.

2 Drawing Sheets

Botanical designation: *Osteospermum ecklonis.*
Cultivar denomination: 'SUNOST1502'.

CROSS-REFERENCED TO CLOSELY RELATED APPLICATIONS

Title: *Osteospermum* Plant Named 'SUNOST1501'.
Applicant: Bjarne Nyholm Larsen.
Filed: Dec. 31, 2015 having U.S. Plant patent application Ser. No. 14/998,430.

BACKGROUND OF THE INVENTION

The present invention relates to a new and distinct cultivar of *Osteospermum* plant, botanically known as *Osteospermum ecklonis* and hereinafter referred to by the name 'SUNOST1502'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive ray and disc floret coloration.

The new *Osteospermum* plant originated from a cross-pollination by the Inventor in May, 2011 of *Osteospermum ecklonis* 'SUNOST1103', disclosed in U.S. Plant Pat. No. 23,450, as the female, or seed, parent with a proprietary selection of *Osteospermum ecklonis* identified as code number 09.20.023, not patented, as the male, or pollen, parent. The new *Osteospermum* plant was discovered and selected by the Inventor as a single flowering plant within the progeny of the stated cross-pollination in a controlled greenhouse environment in Odense, Denmark in June, 2012.

Asexual reproduction of the new *Osteospermum* plant by terminal cuttings in a controlled greenhouse environment in Odense, Denmark since September, 2012 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SUNOST1502'. These characteristics in combination distinguish 'SUNOST1502' as a new and distinct *Osteospermum* plant:

1. Upright and mounding plant habit.
2. Freely branching growth habit.
3. Freely flowering habit.
4. Large daisy-type inflorescences with dark orange red-colored ray florets with that are dark red in color towards the base.
5. Good garden performance.

Plants of the new *Osteospermum* differ primarily from plants of the female parent, 'SUNOST1103', in the following characteristics:

1. Plants of the new *Osteospermum* are more upright than plants of 'SUNOST1103'.

2. Plants of the new *Osteospermum* and 'SUNOST1103' differ in ray floret color as plants of 'SUNOST1103' have purple-colored ray florets.

Plants of the new *Osteospermum* differ primarily from plants of the male parent selection in the following characteristics:

1. Plants of the new *Osteospermum* are more upright than plants of the male parent selection.
2. Plants of the new *Osteospermum* and the male parent selection differ in ray floret color as plants of the male parent selection have dusty orange-colored ray florets.

Plants of the new *Osteospermum* can be compared to plants of the *Osteospermum ecklonis* 'SUNOST1501', disclosed in U.S. Plant patent application Ser. No. 14/998,430 filed concurrently. In side-by-side comparisons conducted in Odense, Denmark, plants of the new *Osteospermum* differed from plants of 'SUNOST1501' in the following characteristics:

1. Plants of the new *Osteospermum* were more upright than plants of 'SUNOST1501'.
2. Plants of the new *Osteospermum* and 'SUNOST1501' differed in ray floret color as plants of 'SUNOST1501' had orange red-colored ray florets that are purple in color towards the base.

Plants of the new *Osteospermum* can also be compared to plants of the *Osteospermum ecklonis* 'SUNOST1204', disclosed in U.S. Plant Pat. No. 25,554. In side-by-side comparisons conducted in Odense, Denmark, plants of the new *Osteospermum* differed from plants of 'SUNOST1204' in the following characteristics:

1. Plants of the new *Osteospermum* had larger leaves than plants of 'SUNOST1204'.
2. Plants of the new *Osteospermum* and 'SUNOST1204' differed in ray floret color as plants of 'SUNOST1204' had bright golden orange-colored ray florets.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph on the first sheet comprises a side perspective view of a typical flowering plant of 'SUNOST1502' grown in a container.

The photograph on the second sheet is a close-up view of a typical flowering plant of 'SUNOST1502'.

DETAILED BOTANICAL DESCRIPTION

The aforementioned photographs, following observations and measurements describe plants grown during the winter in 11-cm containers in a glass-covered greenhouse in Odense, Denmark and under cultural practices typical of commercial *Osteospermum* production. During the production of the plants, day temperatures ranged from 14° C. to 20° C. and night temperatures averaged 14° C. Plants were pinched one time and were 14 weeks old when the photographs and description were taken. In the following description, color references are made to The Royal Horticultural Society Colour Chart, 2007 Edition, except where general terms of ordinary dictionary significance are used.

Botanical classification: *Osteospermum ecklonis* 'SUNOST1502'.

Parentage:

*Female, or seed, parent.*—*Osteospermum ecklonis* 'SUNOST1103', disclosed in U.S. Plant Pat. No. 23,450.

*Male, or pollen, parent.*—Proprietary selection of *Osteospermum ecklonis* identified as code number 09.20.023, not patented.

Propagation:

*Type.*—Terminal vegetative cuttings.

*Time to initiate roots, summer.*—About twelve days at temperatures about 18° C.

*Time to initiate roots, winter.*—About 14 days at temperatures about 18° C. to 20° C.

*Time to produce a rooted cutting, summer.*—About 20 days at temperatures about 18° C. to 20° C.

*Time to produce a rooted cutting, winter.*—About 28 days at temperatures about 18° C.

*Root description.*—Medium in thickness, fibrous; typically whitish in color, actual color of the roots is dependent on substrate composition, water quality, fertilizers, substrate temperature and physiological age of roots.

*Rooting habit.*—Freely branching; medium density.

Plant description:

*Plant and growth habit.*—Upright and mounding plant habit; inflorescences positioned above and beyond the foliar plane on strong peduncles; moderately vigorous growth habit.

*Plant height.*—About 23.1 cm.

*Plant diameter.*—About 21.9 cm.

*Lateral branches.*—Quantity per plant: Freely branching habit with about five primary branches developing per plant, each primary branch with about four secondary branches; pinching enhances branching potential. Length: About 6.5 cm. Diameter: About 4.5 mm. Internode length: About 5 mm. Strength: Strong. Texture and luster: Smooth, glabrous; slightly glossy. Color: Close to 144B.

*Leaf description.*—Arrangement: Alternate, simple; sessile. Length: About 6.4 cm. Width: About 2.7 cm. Shape: Obovate. Apex: Obtuse to broad and blunt acute. Base: Long attenuate. Margin: Irregularly, coarsely and deeply serrate to crenate. Texture and luster, upper surface: Smooth, glabrous except along margins, pubescent; moderately glossy. Texture and luster, lower surface: Pubescent; moderately glossy. Venation pattern: Pinnate, arcuate. Color: Developing leaves, upper surface: Close to between 137B and 143A. Developing leaves, lower surface: Close to 144A. Fully expanded leaves, upper surface: Close to N137B; venation, close to 144B. Fully expanded leaves, lower surface: Close to between 137C and 147B; venation, close to 144B.

Inflorescence description:

*Appearance.*—Daisy-type inflorescence form with oblanceolate-shaped ray florets; inflorescences terminal and axillary and positioned above and beyond the foliar plane on strong peduncles; disc and ray florets developing acropetally on a capitulum; inflorescences face mostly upright.

*Flowering habit.*—Freely flowering habit with about 45 inflorescences developing per plant.

*Fragrance.*—Faint, moderately sweet.

*Flowering response*.—In Denmark, plants of the new *Osteospermum* flower continuously from spring to late summer; early flowering habit, plants begin flowering about six to eight weeks after pinching.

*Inflorescence longevity*.—Inflorescences of plants of the new *Osteospermum* last about two to three weeks on the plant; inflorescences not persistent.

*Inflorescence buds*.—Height: About 1.4 cm. Diameter: About 1.2 cm. Shape: Broadly ovate. Color: Close to 137C; towards the base, close to 143C.

*Inflorescence size*.—Diameter: Large, about 6.7 cm. Depth (height): About 2.7 cm. Disc diameter: About 1.6 cm. Receptacle diameter: About 3 mm. Receptacle height: About 3 mm.

*Ray florets*.—Quantity per inflorescence and arrangement: About 30 arranged in about three whorls. Length: About 3.2 cm. Width: About 9 mm. Shape: Oblanceolate; slightly reflexing. Apex: Shallowly emarginate to shallowly praemorse. Base: Attenuate. Margin: Entire. Texture and luster, upper surface: Smooth, glabrous; velvety; matte. Texture and luster, lower surface: Pubescent; moderately glossy. Color: When opening, upper surface: Close to N163D, 168A and 168B; venation and towards the base, close to 179A. When opening, lower surface: Close to 164A and 164B; venation, close to 166B and 177C. Fully opened, upper surface: Close to 171A and 171B; venation and towards the base, darker than 179A; with development, main color becoming closer to 171C and towards the base, close to 179A to 179B. Fully opened, lower surface: Close to 164A; venation, close to 172A.

*Disc florets*.—Quantity per inflorescence and arrangement: About 200 spirally arranged in numerous whorls at the center of the receptacle. Length: About 8 mm. Diameter, apex: About 4 mm. Diameter, base: About 1 mm. Shape: Tubular; apex dentate, five-pointed. Texture and luster, inner surface: Smooth, glabrous; glossy. Texture and luster, outer surface: Smooth, glabrous; matte. Color, immature: Apex: Close to 203A. Mid-section and base: Close to 157A. Color, mature: Apex: Close to 178A. Mid-section: Close to 162D. Base: Close to 156D slightly tinged with close to 186D.

*Phyllaries*.—Quantity per inflorescence and arrangement: About 32 arranged in about two whorls. Length: About 1.4 cm. Width: About 1.5 mm. Shape: Lanceolate. Apex: Narrowly acute. Base: Cuneate. Margin: Entire. Texture and luster, upper surface: Smooth, glabrous; glossy. Texture and luster, lower surface: Smooth, glabrous; matte. Color, upper surface: Close to 138B. Color, lower surface: Close to 143B.

*Peduncles*.—Length, terminal peduncle: About 11.8 cm. Diameter, terminal peduncle: About 2 mm. Strength: Strong. Aspect, terminal peduncles: Mostly upright. Texture: Moderately pubescent. Color: Close to 143B.

*Reproductive organs*.—Androecium: Present on disc florets only. Quantity per floret: About five. Filament length: About 2 mm. Anther shape: Lanceolate. Anther length: About 2 mm. Anther color: Close to 202A. Pollen amount: Scarce. Pollen color: Close to N25B. Gynoecium: Present on both ray and disc florets. Pistil length: About 4.5 mm. Stigma shape: Bi-parted. Stigma color: Close to N77B. Style length: About 2.5 mm. Style color: Close to N77D. Ovary color: Close to 145D.

*Seeds and fruits*.—Seed and fruit development has not been observed on plants of the new *Osteospermum*.

Disease & pest resistance: Plants of the new *Osteospermum* have not been shown to be resistant to pathogens and pests common to *Osteospermum* plants.

Garden performance: Plants of the new *Osteospermum* have been observed to have good garden performance and to tolerate rain, wind, high temperatures about 40° C. and to be hardy to USDA Hardiness Zone 9.

It is claimed:

1. A new and distinct *Osteospermum* plant named 'SUNOST1502' as illustrated and described.

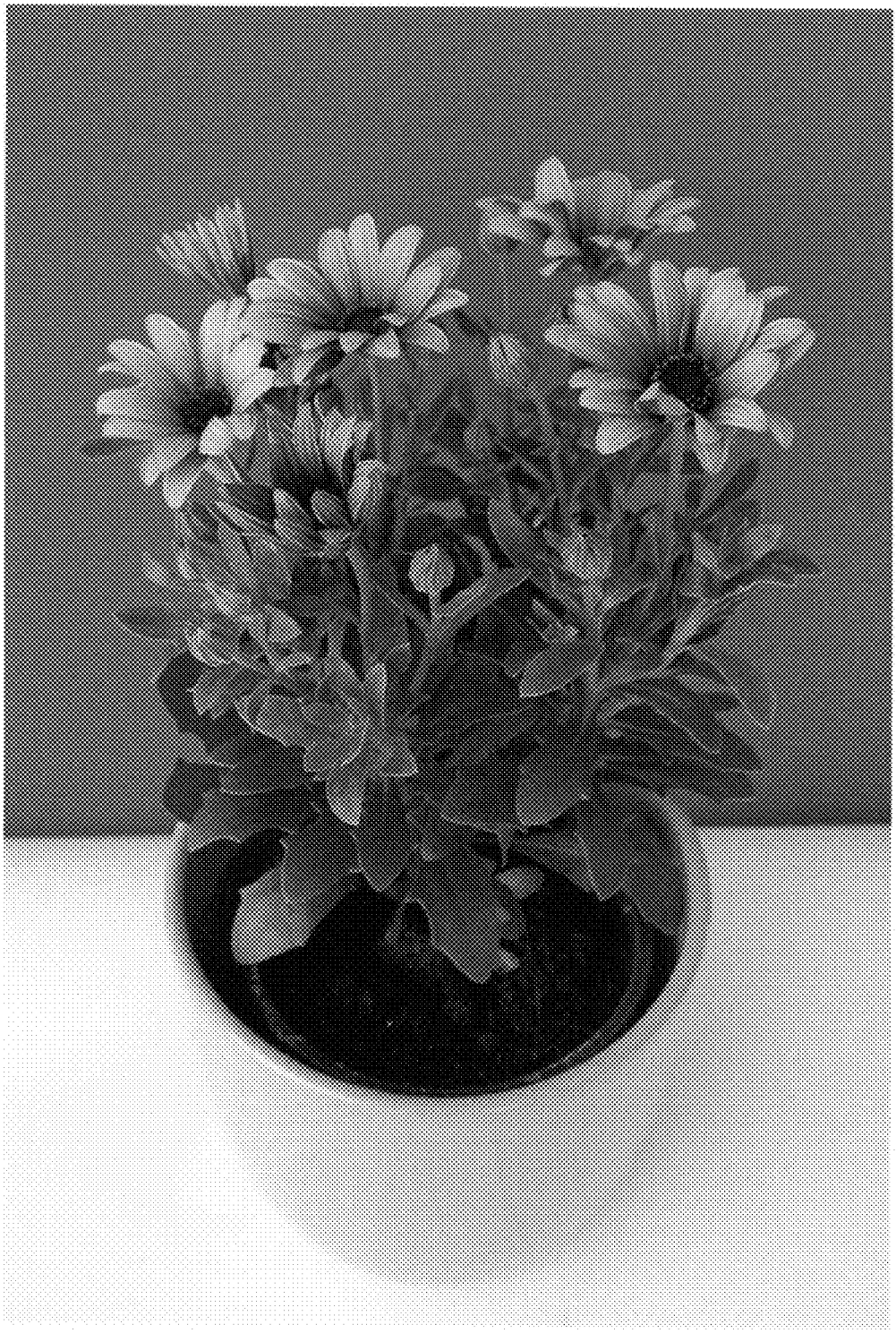

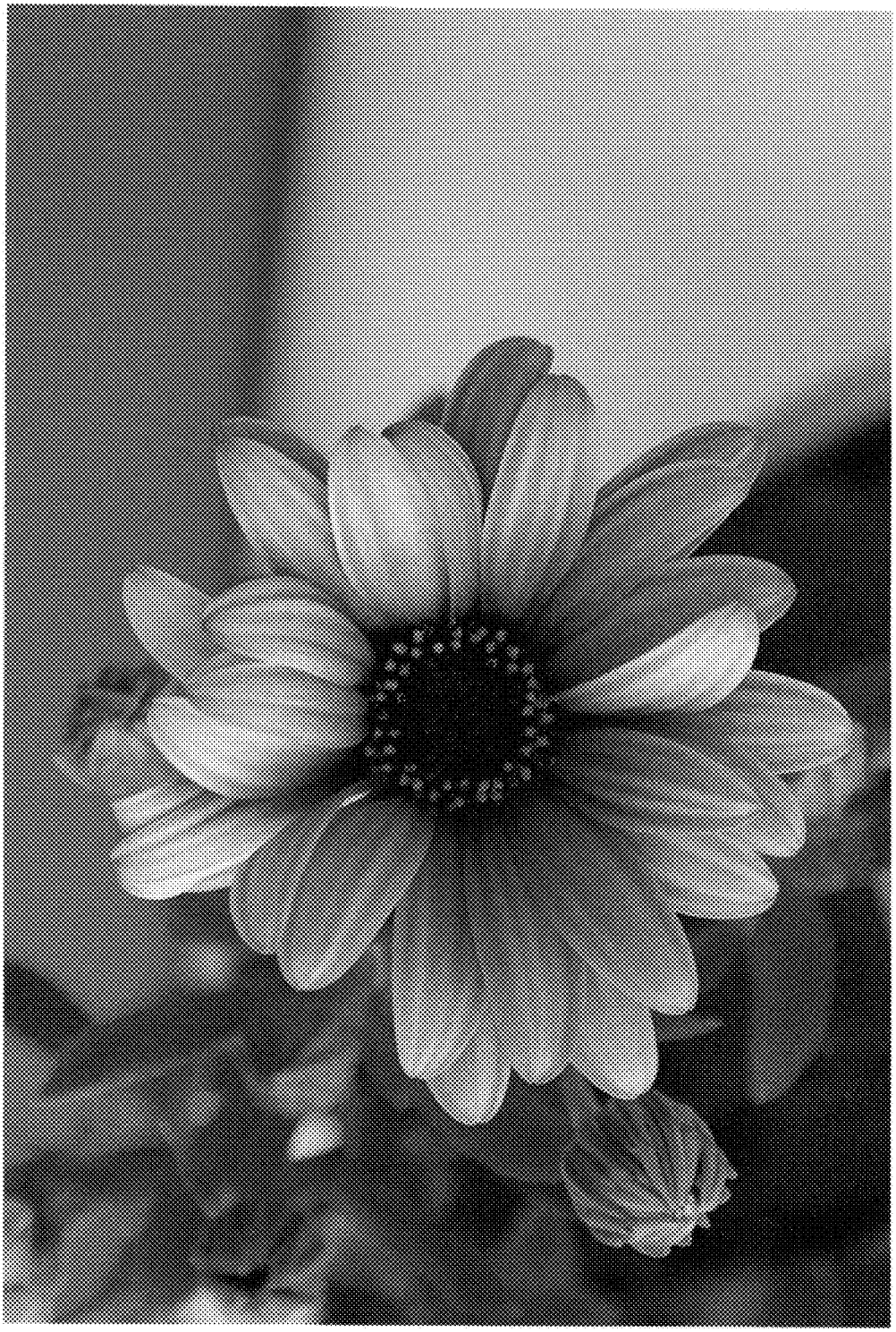

* * * * *